(12) United States Patent
Pellegrino et al.

(10) Patent No.: US 9,498,263 B2
(45) Date of Patent: Nov. 22, 2016

(54) PROSTHETIC LIGAMENT HAVING A HELICAL BONE FASTENER

(71) Applicant: DePuy Synthes Products, Inc., Raynham, MA (US)

(72) Inventors: Richard Pellegrino, Leesburg, VA (US); Christine Rusbarksy, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 69 days.

(21) Appl. No.: 14/067,208

(22) Filed: Oct. 30, 2013

(65) Prior Publication Data

US 2014/0058453 A1 Feb. 27, 2014

Related U.S. Application Data

(60) Continuation of application No. 13/309,462, filed on Dec. 1, 2011, now Pat. No. 8,591,579, which is a division of application No. 11/139,961, filed on May 27, 2005, now Pat. No. 8,092,528.

(51) Int. Cl.
*A61F 2/08* (2006.01)
*A61F 2/44* (2006.01)
(Continued)

(52) U.S. Cl.
CPC ....... *A61B 17/7082* (2013.01); *A61B 17/7022* (2013.01); *A61B 17/869* (2013.01); *A61B 17/8875* (2013.01); *A61F 2/0811* (2013.01);
(Continued)

(58) Field of Classification Search
USPC ....... 606/61, 69, 73, 86, 151, 157, 213, 232, 606/60, 246, 248, 250, 271, 275, 300, 301, 606/315; 623/6.39, 13.11, 13.14, 17.11, 623/17.16, 13.15
See application file for complete search history.

(56) References Cited

U.S. PATENT DOCUMENTS

| 3,988,783 A | 11/1976 | Treace |
| 4,105,034 A | 8/1978 | Shalaby |

(Continued)

FOREIGN PATENT DOCUMENTS

| EP | 0520177 | 12/1992 |
| NL | 1009471 | 12/1999 |
| WO | WO 0067651 | 11/2000 |
| WO | 00/74605 A1 | 12/2000 |
| WO | WO 02067793 | 9/2002 |
| WO | WO 02078574 | 10/2002 |

OTHER PUBLICATIONS

Arthrex Advertisement, Journal of Bone & Joint Surgery, Jan. 2005, vol. 87A No. 1, Journal of Bone & Joint Surgery, Inc., USA.

(Continued)

*Primary Examiner* — Yashita Sharma
(74) *Attorney, Agent, or Firm* — Nutter McClennen & Fish LLP (57) ABSTRACT

An intervertebral connection system wherein the bone anchor has a helical configuration. Also included is a method of installing a bone fastening connection system, comprising the steps of:
a) forming a pilot hole in a bone,
b) providing a connection system comprising a conformable ligament having a first end portion, and an anchor having a central axis which is axially implantable into a bone in a patient's body,
c) inserting the distal head portion of the system into the pilot hole, and
d) rotating the helix to drive the system into the bone and drive the ligament up the helix.

11 Claims, 7 Drawing Sheets

(51) Int. Cl.
  *A61B 17/04* (2006.01)
  *A61B 17/70* (2006.01)
  *A61B 17/86* (2006.01)
  *A61B 17/88* (2006.01)

(52) U.S. Cl.
  CPC .............. *A61F 2/44* (2013.01); *A61B 17/8886* (2013.01); *A61F 2002/0864* (2013.01); *A61F 2002/0888* (2013.01)

(56) References Cited

U.S. PATENT DOCUMENTS

| | | | |
|---|---|---|---|
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 4,570,624 A | 2/1986 | Wu | |
| 4,863,476 A | 9/1989 | Shepperd | |
| 5,049,155 A | 9/1991 | Bruchman | |
| 5,108,431 A | 4/1992 | Mansat | |
| 5,197,983 A | 3/1993 | Berman | |
| 5,464,929 A | 11/1995 | Bezwada | |
| 5,522,899 A | 6/1996 | Michelson | |
| 5,562,671 A | 10/1996 | Goble | |
| 5,591,235 A | 1/1997 | Kuslich | |
| 5,595,751 A | 1/1997 | Bezwada | |
| 5,597,579 A | 1/1997 | Bezwada | |
| 5,607,687 A | 3/1997 | Bezwada | |
| 5,618,552 A | 4/1997 | Bezwada | |
| 5,620,698 A | 4/1997 | Bezwada | |
| 5,643,319 A | 7/1997 | Green | |
| 5,645,850 A | 7/1997 | Bezwada | |
| 5,648,088 A | 7/1997 | Bezwada | |
| 5,665,122 A | 9/1997 | Kambin | |
| 5,681,310 A | 10/1997 | Yuan et al. | |
| 5,698,213 A | 12/1997 | Jamiolkowski | |
| 5,700,583 A | 12/1997 | Jamiolkowski | |
| 5,766,221 A | 6/1998 | Benderev et al. | |
| 5,769,894 A | 6/1998 | Ferragamo | |
| 5,800,543 A | 9/1998 | McLeod et al. | |
| 5,859,150 A | 1/1999 | Jamiolkowski | |
| 5,865,846 A | 2/1999 | Bryan | |
| 5,865,848 A | 2/1999 | Baker | |
| 5,989,256 A | 11/1999 | Kuslich | |
| 6,045,579 A | 4/2000 | Hochshuler et al. | |
| 6,086,589 A | 7/2000 | Kuslich | |
| 6,090,998 A | 7/2000 | Grooms | |
| 6,093,205 A | 7/2000 | McLeod | |
| 6,126,689 A | 10/2000 | Brett | |
| 6,136,001 A | 10/2000 | Michelson | |
| 6,176,882 B1 | 1/2001 | Biedermann et al. | |
| 6,187,009 B1 | 2/2001 | Herzog | |
| 6,296,656 B1 | 10/2001 | Bolduc | |
| 6,332,894 B1 | 12/2001 | Stalcup et al. | |
| 6,336,940 B1 | 1/2002 | Graf | |
| 6,379,361 B1 | 4/2002 | Beck, Jr. | |
| 6,387,130 B1 | 5/2002 | Stone et al. | |
| 6,413,278 B1 | 7/2002 | Marchosky | |
| 6,447,517 B1 | 9/2002 | Bowman | |
| 6,554,852 B1 | 4/2003 | Oberlander | |
| 6,562,073 B2 | 5/2003 | Foley | |
| 6,576,017 B2 | 6/2003 | Foley | |
| 6,595,998 B2 | 7/2003 | Johnson et al. | |
| 6,599,320 B1 | 7/2003 | Kuslich | |
| 6,616,694 B1 | 9/2003 | Hart | |
| 6,652,585 B2 | 11/2003 | Lange | |
| 6,656,184 B1 | 12/2003 | White | |
| 6,733,535 B2 | 5/2004 | Michelson | |
| 6,752,831 B2 | 6/2004 | Sybert | |
| 6,835,208 B2 | 12/2004 | Marchosky | |
| 7,022,129 B2 * | 4/2006 | Overaker et al. | 606/232 |
| 7,104,999 B2 | 9/2006 | Overaker | |
| 7,326,248 B2 | 2/2008 | Michelson | |
| 7,503,920 B2 | 3/2009 | Siegal | |
| 7,655,010 B2 | 2/2010 | Serhan et al. | |
| 7,666,226 B2 | 2/2010 | Schaller | |
| 7,670,374 B2 | 3/2010 | Schaller | |
| 7,703,727 B2 | 4/2010 | Selness | |
| 7,731,751 B2 | 6/2010 | Butler et al. | |
| 7,785,368 B2 | 8/2010 | Schaller | |
| 7,799,081 B2 | 9/2010 | McKinley | |
| 7,837,734 B2 | 11/2010 | Zucherman et al. | |
| 7,850,733 B2 | 12/2010 | Baynham et al. | |
| 7,918,874 B2 | 4/2011 | Siegal | |
| 7,942,903 B2 | 5/2011 | Moskowitz et al. | |
| 8,007,535 B2 | 8/2011 | Hudgins et al. | |
| 8,057,544 B2 | 11/2011 | Schaller | |
| 8,092,528 B2 | 1/2012 | Pellegrino et al. | |
| 8,105,382 B2 | 1/2012 | Olmos et al. | |
| 8,206,423 B2 | 6/2012 | Siegal | |
| 8,262,666 B2 | 9/2012 | Baynham et al. | |
| 8,267,939 B2 | 9/2012 | Cipoletti et al. | |
| 8,343,193 B2 | 1/2013 | Johnson et al. | |
| 8,366,777 B2 | 2/2013 | Matthis et al. | |
| 8,403,990 B2 | 3/2013 | Dryer et al. | |
| 8,454,617 B2 | 6/2013 | Schaller et al. | |
| 8,579,981 B2 | 11/2013 | Lim et al. | |
| 8,591,579 B2 | 11/2013 | Pellegrino et al. | |
| 8,961,609 B2 | 2/2015 | Schaller | |
| 2001/0007957 A1 | 7/2001 | Martin | |
| 2002/0040241 A1 | 4/2002 | Jarvinen | |
| 2002/0120270 A1 | 8/2002 | Trieu | |
| 2002/0123750 A1 | 9/2002 | Eisermann | |
| 2002/0143329 A1 | 10/2002 | Serhan | |
| 2003/0028251 A1 | 2/2003 | Mathews | |
| 2003/0078668 A1 | 4/2003 | Michelson | |
| 2003/0078669 A1 | 4/2003 | Martin | |
| 2003/0088251 A1 | 5/2003 | Braun | |
| 2003/0130735 A1 | 7/2003 | Rogalski | |
| 2003/0135275 A1 | 7/2003 | Garcia et al. | |
| 2003/0139812 A1 | 7/2003 | Garcia et al. | |
| 2003/0171811 A1 | 9/2003 | Steiner | |
| 2003/0187444 A1 | 10/2003 | Overaker | |
| 2003/0187446 A1 | 10/2003 | Overaker | |
| 2003/0195514 A1 | 10/2003 | Trieu | |
| 2003/0229350 A1 | 12/2003 | Kay | |
| 2004/0002761 A1 | 1/2004 | Rogers et al. | |
| 2004/0082956 A1 | 4/2004 | Baldwin | |
| 2004/0087947 A1 | 5/2004 | Lim et al. | |
| 2004/0267278 A1 | 12/2004 | Overaker | |
| 2005/0119752 A1 | 6/2005 | Williams et al. | |
| 2006/0122701 A1 | 6/2006 | Kiester | |
| 2006/0142858 A1 | 6/2006 | Colleran et al. | |
| 2006/0235426 A1 | 10/2006 | Lim et al. | |
| 2006/0276895 A1 | 12/2006 | Pellegrino et al. | |
| 2007/0055272 A1 | 3/2007 | Schaller | |
| 2007/0093901 A1 | 4/2007 | Grotz et al. | |
| 2012/0143333 A1 | 6/2012 | Pellegrino et al. | |
| 2012/0310352 A1 | 12/2012 | DiMauro et al. | |
| 2013/0190875 A1 | 7/2013 | Shulock et al. | |

OTHER PUBLICATIONS

Allcock, "Polyphosphazenes"; The Encyclopedia o/Polymer Science; 1988; pp. 31-41; vol. 13; Wiley Intersciences, John Wiley & Sons.

Cohn, " Biodegradable PEOjPLA Block Copolymers";]ournal o/Biomedical Materials Research; 1988; pp. 993-1009; vol. 22; John Wiley & Sons, Inc.

Cohn, "Polymer Preprints";]ournal o/Biomaterials Research; 1989; p. 498; Biomaterials Research Labortatory, Casali Institute of Applied Chemistry,Israel.

Kemnitzer, "Degradable Polymers Derived From the Amino Acid LTyrosine"; 1997; pp. 251-272; edited by Domb, et. al., Hardwood Academic Press.

Heller, "Poly (Otrho Esters)"; *Handbook o/Biodegradable Polymers*; edited by Domb; et al; Hardwood Academic Press; 1997; pp. 99-118.

Vandorpe, "Biodegradable Polyphosphazenes for Biomedical Applications"; *Handbook o/Biodegradable Polymers*; 1997; pp. 161-182; Hardwood Academic Press.

\* cited by examiner

PROSTHETIC LIGAMENT HAVING A HELICAL BONE FASTENER

CONTINUING DATA

This continuing patent application claims priority from divisional patent application U.S. Ser. No. 13/309,462, filed Dec. 1, 2011, entitled "Intervertebral Ligament having a Helical Bone Fastener" which claims priority from U.S. Ser. No. 11/139,961, filed May 27, 2005, entitled "Intervertebral Ligament having a Helical Bone Fastener" (now U.S. Pat. No. 8,092,528), the specifications of which are incorporated by reference in their entireties.

BACKGROUND OF THE INVENTION

Single level spine fusion procedure typically entails removing the intervertebral disk (not shown) and inserting an interbody device into the disk space.

Current spine fusion procedures rely heavily on the use of posterior fixation to achieve the stability and rigidity necessary to obtain successful clinical results. However, implantation of posterior instrumentation necessarily involves removing important musculoskeletal elements.

Because of these concerns, anterior fixation systems have also been developed which require removal of much less musculoskeletal mass. However, because anterior fixation, especially in the abdominal or thoracic area, lies in close proximity to vital internal organs such as the aorta, these fixation systems must also possess a low profile.

In general, conventional intervertebral connection systems can be characterized by ligament components which are either a) relatively rigid, or b) not shaped for cooperative connection to bone fasteners, or by bone fasteners which are shouldered to seat upon the vertebral surface. When the ligament is relatively rigid, it must essentially fully lie upon the anterior surfaces of the adjacent vertebrae, thereby limiting design options. Systems having relatively rigid ligaments typically have transverse holes near their end portions for accepting bone fasteners. In systems in which the ligament is not shaped for cooperative attachment to the bone fastener, attachment is typically made by either suturing or by passing a screw through the ligament. When the bone fastener is seated upon the vertebral surface, a portion of the bone fastener protrudes from the surface and the tension of the ligament cannot be further adjusted.

US Patent Application No. 2002/0143329 ("Serhan") discloses a system in which a ligament has conformable portions and end portions shaped to cooperatively connect to shoulderless bone fasteners. The shoulderless feature of the bone fastener allows the bone fastener to be fully driven into the vertebral surface, thereby eliminating any problematic protrusion while also providing a means to adjust the tension of the ligament after the bone fasteners have been located. The conformable portions of the ligament allow the ligament to conform to the recess produced by a fully driven bone fastener without generating undue stress, thereby accommodating the surgeon's desire to fully drive the bone fastener within the recess. The cooperative shape of the ligament end portions allows for non-destructive attachment of the ligament to the bone fasteners without the use of sutures, thereby minimizing unwanted connection-related stresses and undesirable generation of foreign particles within the patient.

However, in many embodiments disclosed in Serhan, the bone fasteners are fixed to the bone by impaction. These impaction forces may compromise the integrity of the bone fastener component.

Moreover, the system disclosed in Serhan requires that the surgeon insert the system under tension and set or hold the tension while deploying the anchoring system. This makes the implantation procedures very arduous, and, due to high impaction forces, may not be suitable for use in certain areas of the spine.

SUMMARY OF THE INVENTION

The present inventors have developed intervertebral connection systems wherein the bone fastener has a helical shape. The helical shape allows installation and anchoring of the tensioning member (ligament) between two vertebral bodies or other bones without applying potential harmful impaction forces.

In preferred embodiments, the helical bone fastener has a hole at its distal end through which an end of the ligament is passed. This allows installation of the system without causing the ligament to twist or bind.

In some embodiments, the ligament is passed through an intermediate portion of the helix and then through the distal hole. When the helix is screwed into the bone when the system is provided in this conformation, the ligament rides up the helix, thereby providing in-situ tensioning of the ligament.

Therefore, in accordance with the present invention, there is provided an anchor having a central axis which is axially implantable into a bone in a patient's body, said anchor comprising:
  a) a distal head portion having a body portion that extends transverse to the central axis of the anchor, a proximal surface, a distal surface, and an axially extending throughhole;
  b) a first helix extending axially from the body portion of the distal head portion and transversely engagable with the bone.

Also in accordance with the present invention, there is provided an intervertebral connection system comprising:
  a) a conformable ligament having a first end portion,
  b) the anchor described above,
wherein the first end portion of the ligament extends through the throughhole of the distal head portion of the anchor.

Also in accordance with the present invention, there is provided a method of installing a bone fastening connection system, comprising the steps of:
  a) forming a pilot hole in a bone,
  b) providing the system described above,
  c) inserting the distal head portion of the system into the pilot hole, and
  d) rotating the helix to drive the system into the bone.

DETAILED DESCRIPTION OF THE INVENTION

Figure 1A:
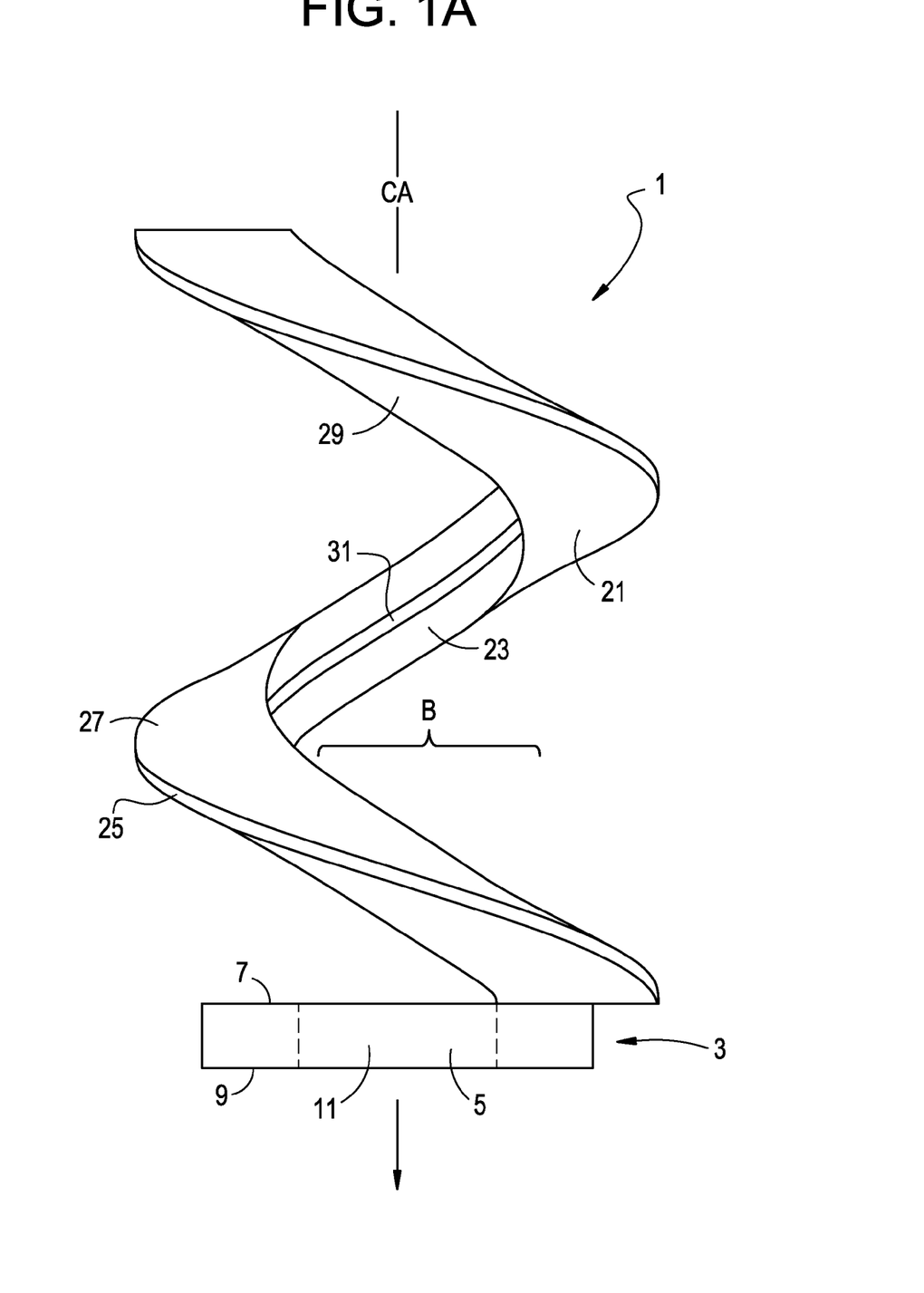
FIG. 1a is a perspective view of the helical bone fastener of the present invention.

Referring now to FIG. 1a, there is provided an anchor having a central axis CA which is axially implantable into a bone in a patient's body, the anchor 1 comprising:
 a) a distal head portion 3 having a body portion 5 that extends transverse to the central axis of the anchor, a proximal surface 7, a distal surface 9, and an axially extending throughhole 11;
 b) a first helix 21 extending axially from the body portion of the distal head portion and transversely engagable with the bone, the first helix having an inner surface 23 defining a bore B, an outer surface 25, and upper 27 and lower 29 middle surfaces, In this particular embodiment, the inner surface 23 of the first helix has a helical groove 31 that extends along the length of the helix. This helical groove defines a helical groove diameter.

In some embodiments, the distal head portion has a first diameter and the first helix has a second diameter, and the first diameter is no greater than the second diameter. This ensures that the helical portion of the anchor will engage bone as the implant is driven into bone.

In some embodiments, the helix has an inner surface having a first thickness and an outer surface having a second thickness, and the first thickness is greater than the second thickness. This provides the helix with a radial sharpness that enhances its ability to engage bone. Preferably, the first thickness of the inner surface is at least three times greater than the second thickness of the outer surface.

Figure 1B:
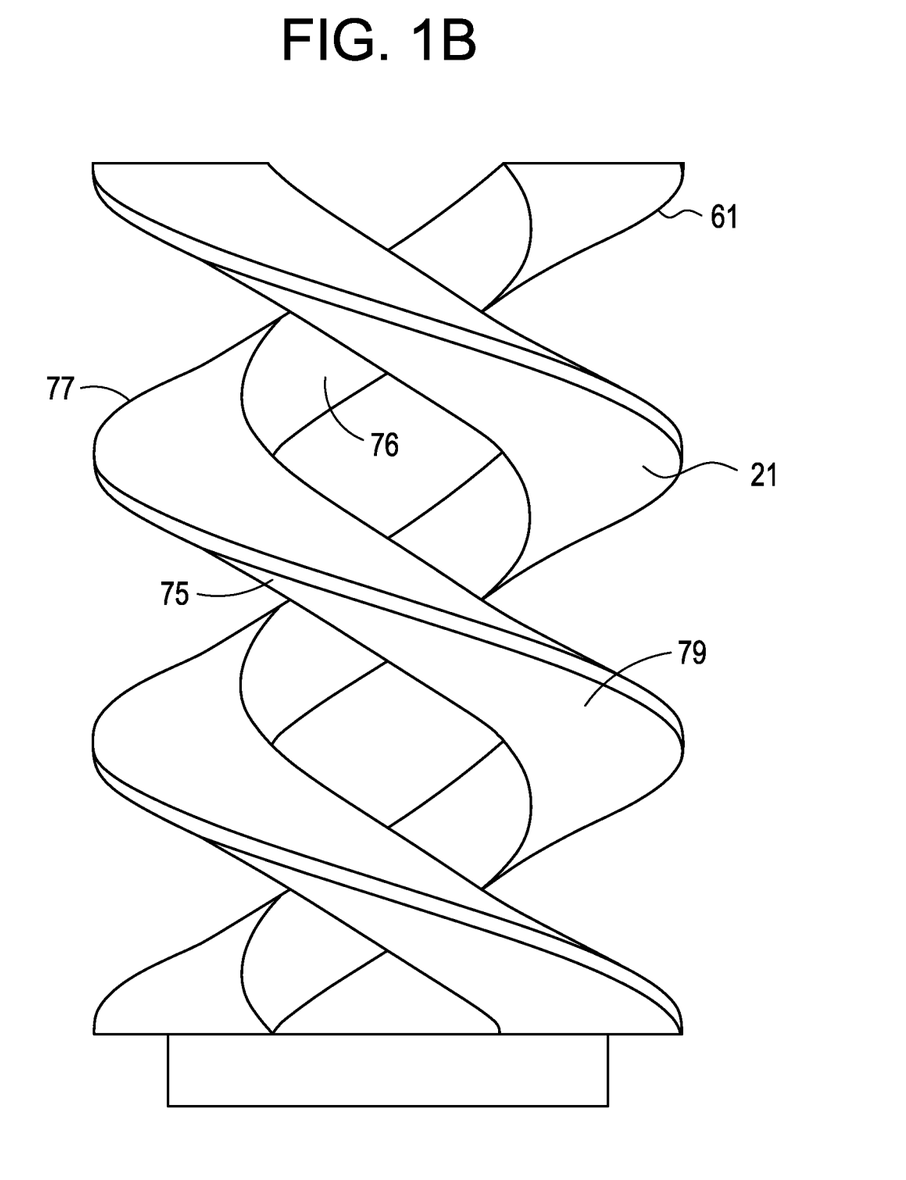
FIG. 1b discloses an alternative double helix design, wherein the helices are not attached.

Now referring to FIG. 1b, there is provided a bone anchor comprising a double helix structure comprising a first helix 21, and a second helix 61 also extending axially from the body portion of the distal head portion, the second having an outer surface 75, an inner surface 76, and upper 77 and lower 79 middle surfaces. FIG. 1b discloses an alternative double helix design, wherein the relative orientation of the helices is fixed by their attachment to the distal head portion of the anchor (i.e., two helices are not attached by a wall).

In soft tissue applications, the flexibility of both the helix and soft tissue are such that the surgeon may simply insert the anchor into the soft tissue without having to engage in a threading procedure. Once inserted, the tool is removed and the tynes will anchor the soft tissue.

Figure 1C:
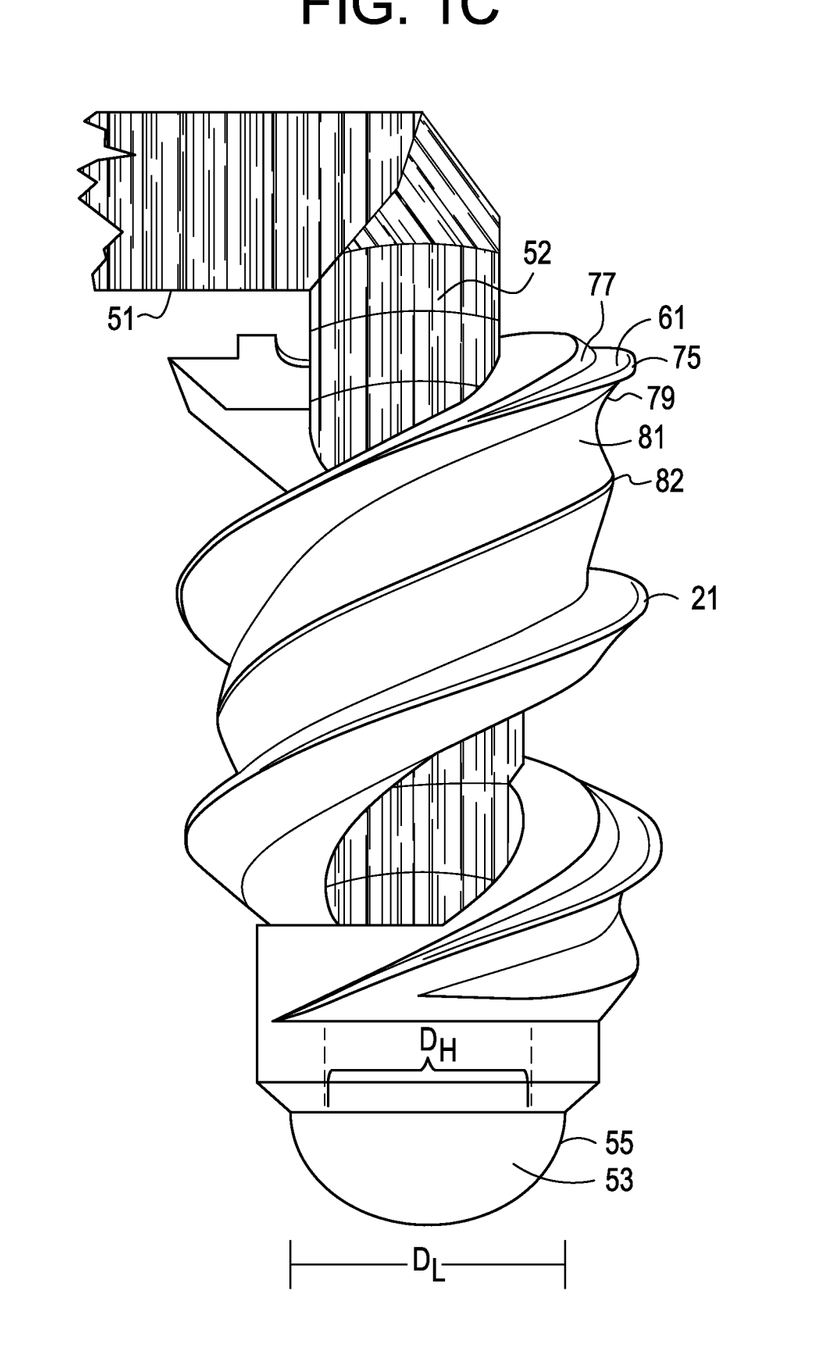
FIG. 1c is a side view of the connection system of the present invention having an attached double helix, and wherein wherein a ligament occupies the bore of the helix.

Now referring to FIG. 1c, there is provided a bone anchor comprising a double helix structure comprising a first helix 21, and a second helix 61 also extending axially from the body portion of the distal head portion, the second having an outer surface 75, an inner surface, and upper 77 and lower 79 middle surfaces. These two helices are attached by a helical wall 81 that attached to the lower surface of the first helix and the upper surface of the second helix. This walled double helix design increases the strength of the helical structure. In some embodiments, the outer surface of the helical wall has a projecting ridge 82 that enhances the strength of the wall. In some embodiments (not shown), the inside wall of the helical wall has a channel corresponding substantially in shape to the projecting ridge, which allows more room for and more mass to be provided to the insertion tool.

FIG. 1c also discloses an intervertebral connection system of the present invention, wherein a conformable ligament 51 having an intermediate portion 52 passing through the bore of the anchor of FIG. 1c, and wherein the first end portion 53 of the ligament extends through the throughhole of the distal head portion of the anchor.

In this particular system, the first end portion 53 of the ligament has a first diameter $D_L$, the throughhole has a second diameter $D_H$, and the first diameter of the first end portion of the ligament is greater than the second diameter of the throughhole. The greater diameter of the first end portion of the ligament insures that the first end portion of the ligament will remain in its distal position vis-a-vis the bone anchor.

Also in this system, the first end portion of the ligament has a taper that increases in the proximal direction. This allows the first end portion of the ligament to pass more easily through the throughhole when the ligament in inserted into the anchor.

In some embodiments, the first end portion of the ligament has an outer surface 55 that is rounded. Preferably, this rounded cap is formed integral with the remainder of the ligament. In others (not shown), the first end portion has a conical taper.

In some embodiments, the first end portion of the ligament has a loop. This allows the surgeon to pass the ligament through the throughhole, and then attach a cross pin to the loop, thereby insuring that a portion of the ligament will remain distal to the anchor.

In other embodiments, the first end portion of the ligament is present in the form of an integral cap.

Figure 2:
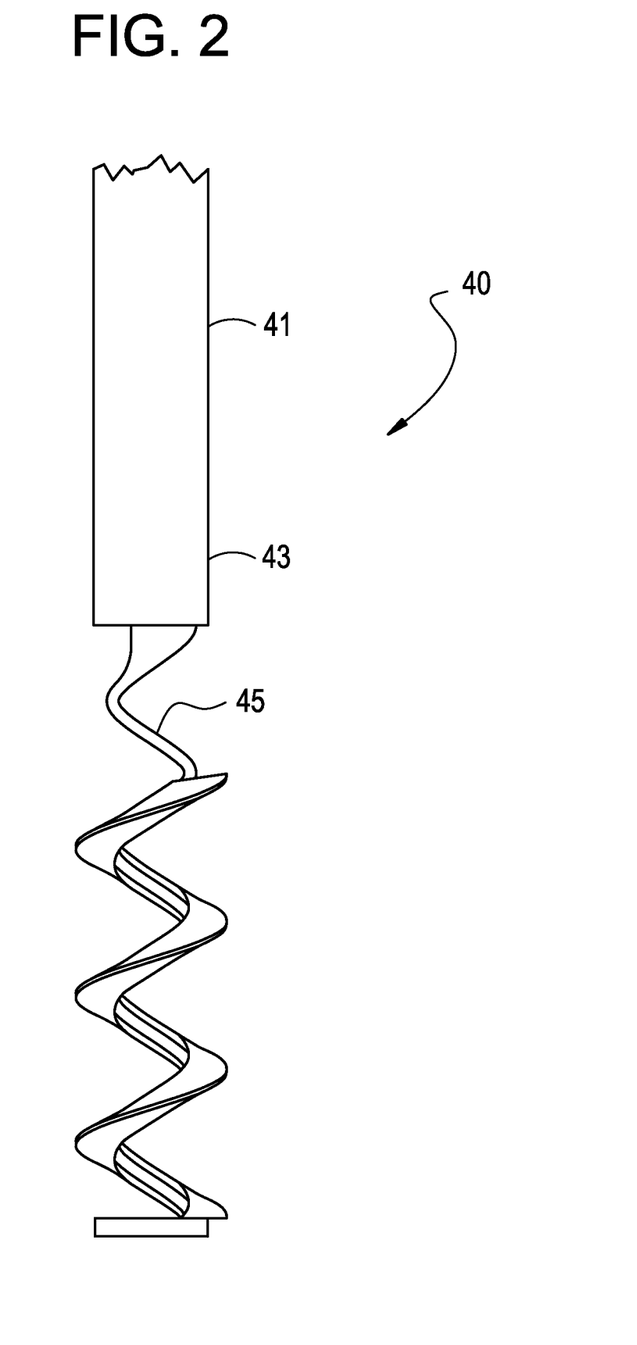
FIG. 2 is a side view of the helical bone fastener of the present invention being held by an insertion tool.

Now referring to FIG. 2, there is provided the helical anchor of FIG. 1 attached to an implantation tool. The tool has a handle 40 comprising a proximal end portion 41 and a distal end portion 43 from which a helical thread 45 extends. The helical thread has an outer diameter that corresponds substantially to the diameter of the helical groove of the inner surface of the first helix, and is designed to mate with the diameter of the helical groove of the inner surface of the first helix, as shown in FIG. 2. This mating allows the surgeon to rotatable drive the anchor into the bone upon rotation of the implantation tool.

Therefore, also in accordance with the present invention, there is provided (claim 20) a kit for implanting a bone anchor, comprising:
 a) an anchor having a central axis which is axially implantable into a bone in a patient's body, said anchor comprising:
  i) a distal head portion having a body portion that extends transverse to the central axis of the anchor, a proximal surface, a distal surface, and an axially extending throughhole;
  ii) a first helix extending axially from the body portion of the distal head portion and transversely engagable with the bone, the first helix having an inner surface having a groove therein, and
 b) an implantation tool comprising:
  i) a handle comprising a proximal end portion and a distal end portion, and
  ii) a helical thread extending from the distal end portion of the handle, the helical thread having an outer diameter, wherein the outer diameter of the helical thread corresponds substantially to the diameter of the helical groove of the inner surface of the first helix.

Figure 3A:
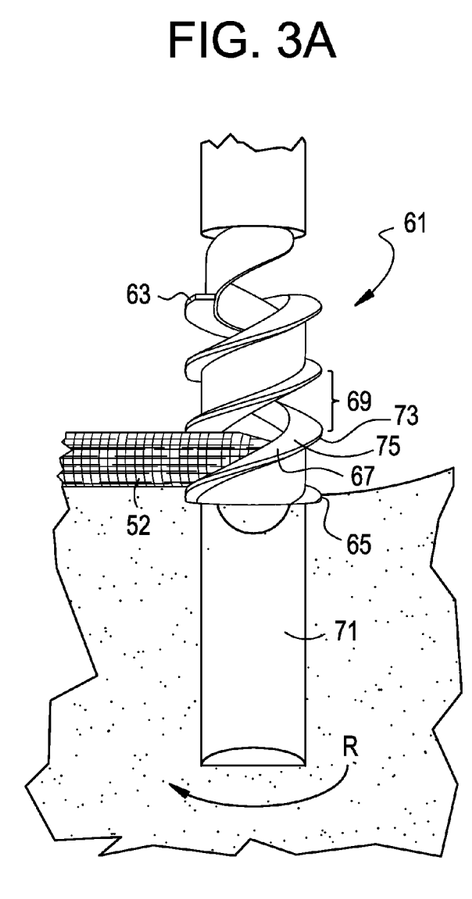
FIGS. 3a-b show a side view of the system of the present invention being driven into a vertebral body by an insertion tool, wherein the tension on the ligament increases as the helix enters the bone.
Figure 3B:
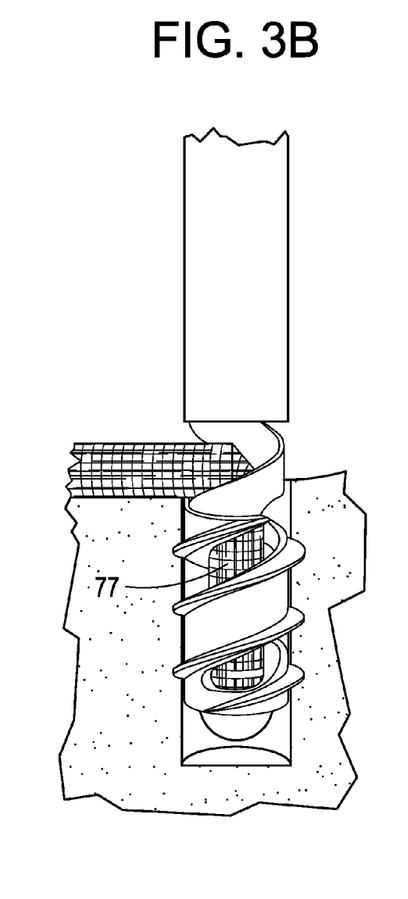

FIGS. 3a-b shows a side view of the system of the present invention being driven into a vertebral body by an insertion tool, wherein the tension on the ligament increases as the helix enters the bone.

Now referring to FIG. 3a, in use, the surgeon first drills a pilot hole 71 having a diameter slightly smaller than the diameter of outer surface 73 of the helical structure. The surgeon then taps the hole with the appropriate tap. Accordingly, when the helical structure is driven down into the tapped hole, the outer surface of the helical structure securely engages the bone.

Also in FIG. 3a, the ligament has an intermediate portion 52, while the helical structure 61 has a proximal end 63, a distal end 65, and an intermediate portion 67. FIG. 3a shows the intermediate portion 52 of the ligament extending through an opening 69 defined within the intermediate portion of the helix.

Still referring to FIG. 3a, when the surgeon rotates the implantation tool (as shown by the arrow R), the helical structure is rotatably driven down into the bone. Moreover, the effect of the rotation upon the intermediate portion of the ligament, which is resting upon an upper surface 75, is to force that portion to climb the upper surface of the helical structure.

Now referring to FIG. 3b, when the surgeon has completed a few revolutions of the implantation tool, the helical structure has not only been driven distally into the bone to provide secure engagement, but a portion 77 of the intermediate portion of the ligament now resides within the bore of the helical structure. Because that portion 77 of the ligament was forced into the bore by the rotation of the helical structure, tension is imparted to the ligament.

Figure 4:
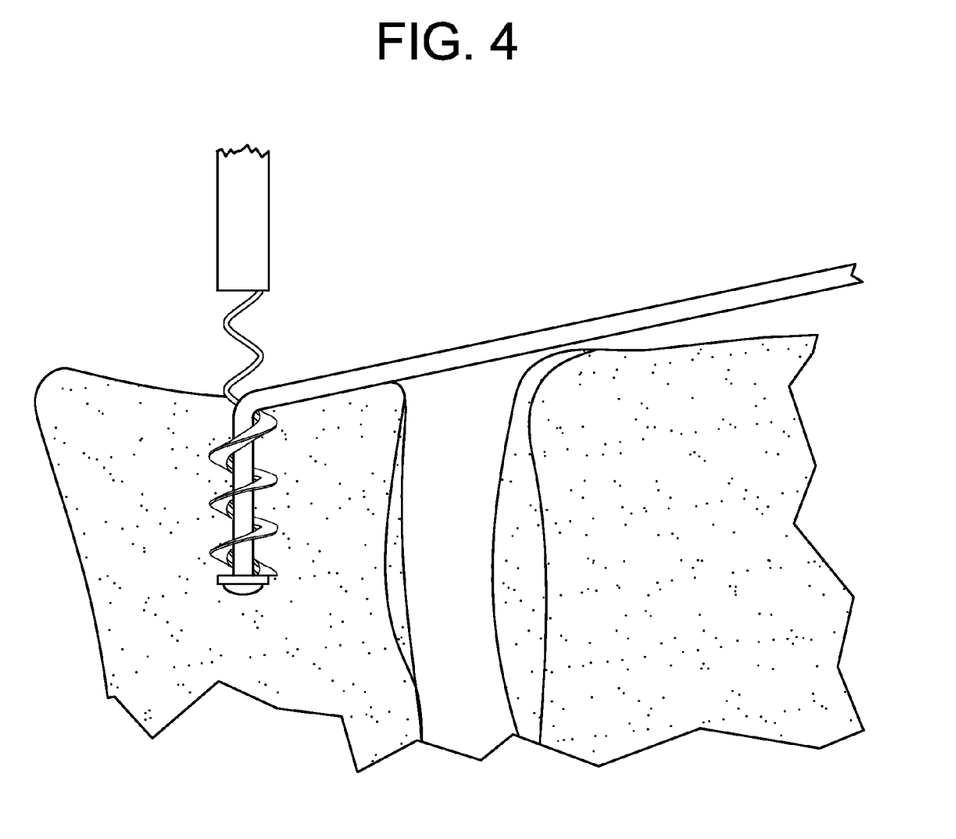
FIG. 4 is a side view of the system of the present invention driven into a vertebral body.
Figure 5:
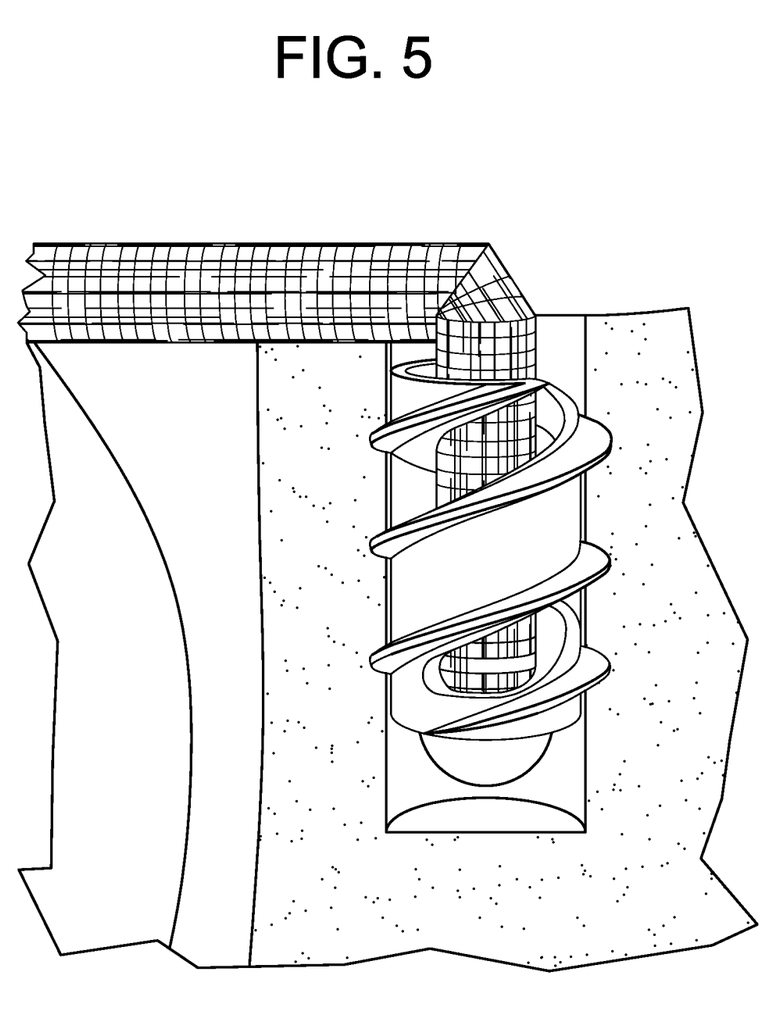
FIG. 5 is a side view of the system of the present invention driven into a vertebral body, wherein the implantation tool is removed.

Now referring to FIG. 4, there is provided a cut-away view of an anchor/ligament combination of the present invention being embedded within a vertebral body. Next, the surgeon would remove the implantation tool by simply counter-rotating it. The resulting implant is shown in FIG. 5. Referring back to FIG. 4, after the implantation tool is removed, the surgeon would follow the same procedure to implant the remaining end of the ligament (second anchor not shown) in the adjacent vertebral body.

In one especially preferred embodiment of the present invention, the system is intended to act as a temporary stabilization system for spine fusion procedures. That is, the system provides only temporary stabilization of the spine until the desired fusion can be achieved. Once fusion has been achieved, the system of this embodiment serves no further purpose.

Therefore, in some embodiments, at least the central portion is made of a bioresorbable material. Preferably, the conformable portions are also made of a bioresorbable material. Preferably, the end portions of the ligament are also made of a bioresorbable material. Also preferably, the bone fasteners are also made of a bioresorbable material.

Preferred bioresorbable materials which can be used to make components of the present invention include bioresorbable polymers or copolymers, preferably selected from the group consisting of hydroxy acids, (particularly lactic acids and glycolic acids; caprolactone; hydroxybutyrate; dioxanone; orthoesters; orthocarbonates; and aminocarbonates. Preferred bioresorbable materials also include natural materials such as chitosan, collagen, cellulose, fibrin, hyaluronic acid; fibronectin, and mixtures thereof. However, synthetic bioresorbable materials are preferred because they can be manufactured under process specifications which insure repeatable properties.

A variety of bioabsorbable polymers can be used to make the device of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, χ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, χ,χ-diethylpropiolactone, ethylene carbonate, ethylene oxalate, 3-methyl-1,4-dioxane-2,5-dione, 3,3-diethyl-1,4-dioxan-2, 5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Preferably, the bioresorbable material is selected from the group consisting of poly(lactic acid) ("PLA") and poly (glycolic acid) ("PGA"), and copolymers thereof. These materials are preferred because they possess suitable strength and biocompatibility, display desirable resorption profiles, and have a long history of safe in vivo use. In general, PLA is a desirable because it typically has a resorption time exceeding 12 months, whereas PGA resorbs fairly quickly (having a resorption time of less than 12 months). However, PLA can require many years to completely resorb, and so is more likely to produce foreign-body reactions. Therefore, more preferably, the material is a PLA/PGA copolymer, more preferably the copolymer comprises between 80 wt % and 99 wt % lactic acid (as PLA), and between 1 wt % and 20 wt % glycolic acid (as PGA). Copolymers within these ranges provide the proper balance between the strength and the resorption time of the ligament.

Preferably, the bioresorbable component retains at least 50% of its tensile strength 6 months after implantation, but loses at least 50% of its tensile strength within 12 months of implantation. When this window of bioresorption is achieved, the component has the strength necessary to carry out its intended purpose during the time when bony fusion is occurring, but also bioresorbs after such fusion normally takes place. Also preferably, the bioresorbable polymer retains at least 50% of its mass 6 months after implantation, but loses at least 90% of its mass within 2 years of implantation. This may be accomplished by use of an 95/5 PLA/PGA copolymer.

In other embodiments, bioresorbable component comprises subintestinal submucosa (SIS).

Although bioresorbable materials are the preferred materials of construction for the components of the present invention, these components may be made from any material appropriate for human surgical implantation, including but not limited to all surgically appropriate metals including titanium, titanium alloy, chrome alloys and stainless steel, and non-metallic materials such as permanent or bioresorbable materials such as carbon fiber materials, resins, plastics and ceramics. If a nonbioresorbable material is selected, then preferred materials include polyesters, (particularly aromatic esters such as polyalkylene terephthalates, polyamides; polyalkenes; poly(vinyl fluoride); polyurethanes; polytetrafluoroethylene PTFE; carbon fibres; silk; and glass, and mixtures thereof.

In one preferred embodiment, both the compressible ligament and the bone fastener are each bioresorbable. The bioresorbable aspect of this device minimizes long term foreign body effects, while the compressible aspect minimizes the chances of short term failure by compressive loading.

In some embodiments, the helical bone fastener may be suitable used in conjunction with the intervertebral connection systems disclosed in US Published patent Application No. 2002/0143329 (Serhan), filed Mar. 30, 2001, the specification of which is hereby incorporated by reference in its entirety.

We claim:

1. A method of installing an implant, comprising the steps of:
 a) forming a pilot hole in a bone,
 b) providing an implant having a central axis which is axially implantable into a bone in a patient's body, said implant comprising:
  i) a first helix extending axially and transversely engagable with the bone, and
  ii) a second helix extending axially and transversely engagable with the bone, and
  iii) a helical wall,
 wherein the first and second helices extend transversely from the helical wall,
 c) inserting the implant into the pilot hole, and
 d) rotating the first and second helices to drive the implant into the bone,
 wherein the implant defines an axially extending throughhole having tissue received therethrough.

2. The method of claim 1, further comprising e) placing a resin within the implant.

3. The method of claim 1, wherein the implant includes an opening between coils of the helical wall.

4. The method of claim 2, wherein the resin comprises a ligament.

5. The method of claim 4, wherein the ligament has a loop configured to receive a cross pin therethrough.

6. The method of claim 1, wherein the tissue comprises a ligament.

7. The method of claim 1, wherein an outer surface of the helical wall has a projecting ridge.

8. The method of claim 7, wherein an inside wall of the helical wall has a channel corresponding substantially in shape to the projecting ridge.

9. The method of claim 1, wherein a first end portion of the tissue extends through the throughhole of the implant.

10. The method of claim 1, further comprising e) placing a bioresorbable material within the implant.

11. The method of claim 10, further comprising f) removing the bioresorbable material from the implant once the implant is secured to the bone.

* * * * *